(12) United States Patent
Rizza et al.

(10) Patent No.: US 9,028,883 B2
(45) Date of Patent: May 12, 2015

(54) COMPOSITIONS FOR THE TREATMENT OF HEMORRHOIDS AND RELATED DISEASES

(75) Inventors: Luisa Rizza, Santa Venerina (IT); Salvatore Munafo, Santa Venerina (IT); Alberto Serraino, Santa Venerina (IT)

(73) Assignee: Bionap Srl, Santa Venerina (IT)

( * ) Notice: Subject to any disclaimer, the term of this patent is extended or adjusted under 35 U.S.C. 154(b) by 235 days.

(21) Appl. No.: 13/393,480

(22) PCT Filed: Sep. 1, 2010

(86) PCT No.: PCT/EP2010/005346
§ 371 (c)(1),
(2), (4) Date: Apr. 4, 2012

(87) PCT Pub. No.: WO2011/026606
PCT Pub. Date: Mar. 10, 2011

(65) Prior Publication Data
US 2012/0183627 A1 Jul. 19, 2012

(30) Foreign Application Priority Data

Sep. 2, 2009 (IT) .............................. MI2009A1523

(51) Int. Cl.
| | | |
|---|---|---|
| A61K 36/00 | (2006.01) | |
| A61K 36/33 | (2006.01) | |
| A01N 43/16 | (2006.01) | |
| A61K 47/10 | (2006.01) | |
| A61K 9/00 | (2006.01) | |
| A61K 9/02 | (2006.01) | |
| A61K 9/48 | (2006.01) | |
| A61K 36/63 | (2006.01) | |

(52) U.S. Cl.
CPC .............. *A61K 47/10* (2013.01); *A61K 9/0031* (2013.01); *A61K 9/02* (2013.01); *A61K 9/4858* (2013.01); *A61K 36/33* (2013.01); *A61K 36/63* (2013.01)

(58) Field of Classification Search
USPC ........................................................ 424/725
See application file for complete search history.

(56) References Cited

U.S. PATENT DOCUMENTS

| | | | | |
|---|---|---|---|---|
| 6,228,387 | B1 * | 5/2001 | Borod ........................... | 424/436 |
| 6,365,198 | B1 * | 4/2002 | Niazi ............................ | 424/725 |
| 6,440,465 | B1 * | 8/2002 | Meisner ....................... | 424/725 |
| 6,849,770 | B2 * | 2/2005 | Guzman et al. ............... | 568/763 |

OTHER PUBLICATIONS

Kroeger Herb ("Kroeger", 1997, Olive Leaf, http://www.kroegerherb.com/index.php/learn/article/135).*
Steven P. Shikiar ("Shikiar", http://www.njsurgery.com/html/Diseases/hemorroids.shtml).*
Mylonaki et al. ("Mylonaki", Anal. Bioanal. Chem 2008, 392, 977-985).*
Jian-Hwa Guo ("Guo", Drug Dev & Deliv., 2004, 4(5), 1-8).*
Vertuani et al. ("Vertuani", Nutrafoods, 2004, 3, 19-26).*
Malainine, M. et al., "Structure and morphology of cladodes and spines of *Opuntia ficus-indica*. Celluslose extraction and characterisation", vol. 51, No. 1, pp. 77-83, Jan. 1, 2003.
Panico, A.M., et al., "Protective effect of *Capparis spinosa* on chondrocytes", vol. 77, No. 20, pp. 2479-2488, Sep. 30, 2005.
Trombetta, D., et al., "Effect of polysaccharides from *Opuntia ficus-indica* (L.) cladodes on the healing of dermal wounds in a rat", vol. 13, No. 5, pp. 352-358, May 9, 2006.
Panico, A.M., "Effect of hyaluronic acid and polysaccharides from *Opuntia ficus indica* (L.) cladodes on the metabolism of human chondrocyte cultures", vol. 111, No. 2, pp. 315-321, Apr. 5, 2007.
Galati, E.M., et al., "*Opuntia ficus indica* (L.) Mill. mucilages show Cytoprotective Effect on Gastric Mucosa in Rat", vol. 21, No. 4, pp. 344-346, Apr. 2007.

* cited by examiner

*Primary Examiner* — Misook Yu
*Assistant Examiner* — Kauser M Akhoon
(74) *Attorney, Agent, or Firm* — Silvia Salvadori, P.C.

(57) ABSTRACT

The present invention relates to pharmaceutical, nutraceutical, health foods and medical device compositions comprising polysaccharides from *Opuntia Ficus Indica* cladodes in combination with antioxidant and anti-inflammatory plant extracts as well as those from Olive leaf, *Capparis Spinosa* buttons, anthocianosides from red oranges, black rice or from other natural sources and their combinations, useful for prevention and therapy of hemorrhoidal disease and related diseases. The invention compositions may be applied topically or administered by oral route.

9 Claims, 4 Drawing Sheets

COMPOSITIONS FOR THE TREATMENT OF HEMORRHOIDS AND RELATED DISEASES

This application is a U.S. national stage of PCT/EP2010/005346 filed on Sep. 1, 2010 which claims priority to and the benefit of Italian Application No. MI2009A001523 filed on Sep. 2, 2009, the contents of which are incorporated herein by reference.

FIELD OF THE INVENTION

The present invention refers to new pharmaceutical, nutraceutical, health foods and medical device compositions for the prevention or the treatment of hemorrhoids, their complications and related illnesses.

More particularly, the present invention is directed to compositions for oral use or topical application comprising polysaccharides from *Opuntia ficus indica* cladodes extract in combination with extracts from olive leaf (*Olea europeaea corticoids*) and optionally with local anesthetics, vasoconstrictors, astringent substances and/or with plant extracts having anti-oxidant or anti-inflammatory effect as well as those from *Capparis Spinosa* buttons, anthocianosides from red oranges, black rice or from other natural sources and their combinations, useful for prevention and therapy of hemorrhoidal disease and related illnesses.

BACKGROUND OF THE INVENTION

Hemorrhoids are anatomical angio-cavernous structures of the anal canal present in utero into adult life that complete liquid and gas continence through blood afflux and deflow, growing in their volume (closing anal canal lumen) because of the arterial afflux, and reducing in their volumee (re-opening the anal canal lumen) because of venous deflow.

Hemorrhoidal disease consists in partial anal canal coating sliding down: rectal mucosa slides down pushing outward internal hemorrhoids which consequently push outward external hemorrhoids.

Hemorrhoids may have hereditary or constitutional etiopathogenesis: however, the cause underlying their development is still unclear. Probably, considering the recurrence of the disease in several family members, sometimes genetic factors are involved. Constipation can make hemorrhoids more serious, because of the irritating effect that hard stools and strong defecation effort may have on the anal canal.

During pregnancy, some of the important changing in the female body promote hemorrhoids and varicose veins incoming or worsening at lower limbs: during pregnancy, in fact, the female body weight increases with negative effects on the venous complex (during pregnancy, in fact, the volume of the uterus increases pushing on abdomen, hampering blood reflux).

Constipation (that may begin or worsening during pregnancy) frequently causes hemorrhoidal disease onset during pregnancy.

In people suffering from constipation, hemorrhoids are often related to anal fissures, tears or ulcers that occur at the end of anal canal because of the strong defecation effort that may determine tissue damage in this region.

Hemorrhoidal disease is very widespread, affecting, both in North America and in Europe, 1 to 10 millions people (Holzheimer R G, *Eur J Med Res*, 26 JAN 2004; 9 (1): 18-36, *Hemerrhoidectomy: indications and risks*), Hemorrhoidal disease is usually treated with strict dietary and behavioural rules and with pharmacological treatments. Most of the people suffering from hemorrhoidal disease are able to live with this disease thank to strict dietary habits and lifestyle, hygiene and/or the use of topical application of products containing steroids (because of their anti-inflammatory action) and local anesthetics.

If necessary, dietary and behavioural rules may be added with a pharmacological treatment with topical application of products (creams, ointments, unguents, foams and suppositories) containing steroids, that acts on pain and swelling, and/or local anesthetics, that relieve itching and pain. However, these products are recommended for brief-term therapies, because long-term treatment with these substances may determine irritation at the application site, particularly at level of rectal and anal mucosa.

When healthy and balanced diet assisted by an appropriate drug treatment is not effective and complicances of the pathology arise, is used for surgical treatment (hemorrhoidectomy, haemorrhoidopexy or prolapsectomy), but this may be followed by post-surgical complications as well as bleeding, fissures, fistulae, abscesses, perianal infections, urinary retention, fecal and urinary incontinence.

Given the hemorrhoidal disease prevalence, especially in pregnant women and in the early postpartum, and considering the spread of its complicances and of related pathologies, is still relevant the finding of a sure and effective treatment for the prevention and the therapy of such diseases, avoiding the patient, at the same time, undergoing to repeated pharmacological and surgical treatments in order to resolve the disease and related symptoms.

DISCLOSURE OF THE INVENTION

New pharmaceutical, dermocosmetic, nutraceutical, health foods and medical device compositions able to reduce the inflammatory component characteristic of hemorrhoidal disease and of its complicances are now identified. These compositions have also a mucoprotective effect and then they are even able to protect anal and rectal mucosa from the irritative effect of substances that may be present in faeces causing pain in the acute phase of the disease and making easy or quickening its relapse.

These compositions are characterised by containing polysaccharides from *Opuntia Ficus Indica* cladodes extract in combination with *Olea europaea* leaf extract having anti-oxidant and/or anti-inflammatory action, and optionally with *Capparis Spinosa* buttons extracts, anthocianosides from red oranges, black rice or from other natural sources and their combinations, for preventing and treating hemorrhoidal disease, its complicances and related illnesses.

As used herein, the term "medical device" refers to an "Active medical device" (class I) in accordance with the Directive 93/42/EEC Annex IX classification.

*Opuntia Ficus Indica* (Nopal) is a plant belonging to Cactaceae, native to Mexico and to south-west United States, but widespread even in self-sown Mediterranean vegetation.

Fruits and younger cladodes (tender) are used from ancient times for dietary use or to prepare alcoholic drinks.

In popular medicine the plant is used in many ways: fruits are thought astringent and were used by sailors, because of their vitamin C wealth, to prevent scorbutus; young cladodes are used as cataplasm—oven warmed—as emollient agents; the use of cladodes pulp on coetaneous wounds and ulcers is an excellent anti-inflammatory, re-epithelialising and healing remedy: its an old Sicilian traditional remedy used still nowadays in the country tradition; the flowers decoction has diuretic properties.

More recently it was observed that: 1) *Opuntia ficus indica* fruits have marked anti-oxidant properties (Tesoriere and al., Supplementation with cactus pear (*Opuntia ficus-indica*) fruit decreases oxidative stress in healthy humans: a comparative study with vitamin. C, Am Clin Nutr, 2004 August; 80(2): 391-395); 2) an *Opuntia ficus indica* extract is effective in the alcohol hangover therapy (Wiese. J and al., *Effect of Opuntia Ficus Indica on symptoms of the alcohol hangovers*. Arch Intern Med. 2004 Jun. 28; 164(12): 1334-1340); 3) the high polysaccharidic fraction concentration in *Opuntia* cladodes, essentially formed by a polymer of galactose, arabinose and other sugars, has swallowed fat and sugars ligand properties (making so them impossible to be absorbed) leading to good results on glyco-lipidic metabolisms and on metabolic syndrome; 4) *Opuntia ficus indica* cladodes mucilages and pectins proved to be gastro-protective in experimental animal models (Vazquez-Ramirez R. and al., *Reversing gastric mucosal alterations during ethanol-induced chronic gastritis in rats by oral administration of Opuntia Ficus Indica mucilage*, World J. Gastroenterol. 2006 Jul. 21; 12(27): 4318-4324).

Trombetta and al. (Trombetta D. and al., *Effects of polysaccharides from Opuntia Ficus Indica (L.) cladodes on the healing of dermal wounds in the rat*, Phytomedicine, 13 (2006)352-358) observed that polysaccharides from *Opuntia ficus indica* cladodes extract have cutaneous healing effect acting on cellular matrix and modulating laminin laying down.

It has now been unexpectedly found that polysaccharides extracted from *Opuntia ficus indica* cladodes produce an anti-inflammatory effect in a synergistic way with *Olea europaea* leaf extract and that this effect is increased by the addition of *Capparis Spinosa* buttons extracts, anthocianosides from red oranges, black rice or from other natural sources and their combinations, whereby the *Opuntia ficus* and *Olea europea* extracts are conveniently used in combination for preventing and treating hemorrhoidal disease, its complications and related illnesses.

According to an invention embodiment, the *Opuntia ficus* and *Olea europea* extracts are provided in the form of a combined preparation for simultaneous or separate use in the prevention and treatment of hemorrhoidal disease, complications thereof and related illnesses, and particularly for use in the mucoprotection of anal and rectal mucosa and to prevent or treat inflammation of the same.

According to the present invention, polysaccharides from *Opuntia ficus indica* cladodes may be in mucilage form, obtained by a pressing process or by treatment in water at room temperature. Alternatively, after the pressing process, cladodes juice is centrifuged and the supernatant is subjected to ultrafiltration leading to an aqueous solution enriched in the MW>$10^4$ Da polysaccharides fraction which may be concentrated and then dried. Polysaccharides content in *Opuntia ficus indica* cladodes extract is from 1 up to 70%.

*Olea europaea* leaf may be extracted with aqueous or hydro-alcoholic solvents (10-80% ethanol), at room temperature or at 60-70° C. The hydro-alcoholic extraction may be repeated in order to obtain an higher biophenols concentration. At the end of the extraction process, the aqueous solvent is removed in vacuum at 40'C.

Furthermore, a higher biophenols concentration may be obtained loading the dried extract on resins, preferably styrenic resins, and eluting with ethanol:water 50:50 (v/v).

*Olea europaea* leaf extract contains phenols (tyrosol, hydroxytyrosol and their derivatives), cinnamic acids, flavonoids (as well as apigenin, luteolin and their glucosidic derivatives, rutin, quercetin), lignans, secoiridoids (as well as oleurosid, oleuropein and their derivatives, elenolic acid), and is characterised by a particular content in polyphenols: flavonoids (apigenin, luteolin and their derivatives) 2-40% (w/w), oleuropein 0.5-10% (w/w) and hydroxytyrosol and derivatives 1-30% (w/w).

The present invention also refers to pharmaceutical, dermocosmetic, nutraceutical, health foods and medical device compositions for oral administration, topical or rectal application, comprising polysaccharides from *Opuntia ficus indica* cladodes extract in combination with *Olea europaea* leaf extract having anti-oxidant and/or anti-inflammatory action, and optionally with *Capparis Spinosa* buttons extracts, anthocianosides from red oranges, black rice or from other natural sources and their combinations, for preventing and treating hemorrhoidal disease, its complicances and related illnesses.

According to the present invention, the terms "combination" and "combined preparation" are used for both fixed and therapeuthic combinations of the extracts or the actives considered. In the first case (fixed combination) the extracts or the actives are contained in the same composition, with vehicles, excipients or other ingredients useful for the proposed applications; in the second case (therapeutic combination) the active ingredients may be administered or applied in separate compositions as well as through different administration routes, in order to obtain a combined therapeutic effect.

The synergistic effect due to the combination of the considered actives or extracts allows advantageously to reduce the inflammatory component combined with hemorrhoidal disease, and, having the considered compositions also a mucoprotective effect, they are able, at the same time, to protect the rectal mucosa, determining a rapid resolution of the synthomps with an higher grade of therapeutic safety, a very important factor in case of repeated treatments, in general for topical treatments and in particular for pregnant or post-partum women and elderly people treatment.

This allows to carry out an effective and safe targeted therapy, suitable to prevent or to cure hemorrhoidal disease and its complicances well as anal fissures—even in combination with other pharmacological or surgical therapies for the same diseases.

Object of the invention is therefore providing pharmaceutical, dermocosmetics, nutraceutical, health foods and medical device oral or topical (rectal) compositions, comprising polysaccharides from *Opuntia ficus indica* cladodes extract in fixed or therapeutic combination with *Olea europaea* leaf extract and optionally with *Capparis Spinosa* buttons extracts, anthocianosides from red oranges, black rice or from other natural sources and their combinations, for preventing and treating hemorrhoidal disease, its complicances and related illnesses (e.g. anal fissures), for preventing relapse in same disease and for protecting rectal mucosa from the irritative effect of some food components that may be present in faeces.

DESCRIPTION OF THE FIGURES

Further characteristics and advantages of the present invention will be more evident from the following description of several embodiments given as non-limiting examples with reference to the figures, wherein, with regard to the claimed compositions:

DETAILED DESCRIPTION OF THE INVENTION

The present invention provides pharmaceutical, dermocosmetics, nutraceutical, health foods and medical device compositions for oral administration or for topical or intrarectal application for treating hemorrhoidal disease and related illnesses (as well as anal fissures) and for relapse prevention of the same pathologies, comprising polysaccharides extracted from *Opuntia ficus indica* cladodes, optionally supported on maltodextrins up to 50% (w/w), in fixed or combination therapy with *Olea europaea* leaf extract having an anti-oxidant and anti-inflammatory action and optionally with *Capparis Spinosa* buttons extracts, anthocianosides from red oranges, black rice or from other natural sources and their combinations, for preventing and treating the same diseases.

Actives from *Olea europaea* leaf extract useful for the claimed compositions may comprise, as non-limiting examples: phenols, (as well as tyroxol, hydroxytyrosol and their derivatives), cinnamic acid, flavonoids (as well as apigenin, luteolin and their glucosidic derivatives, rutin, quercitin), lignans, secoiridoids (as well as oleurosid, oleuropein and their derivatives, elenolic acid).

The claimed compositions may be liquid, solid or semi-solid, able to be administered per os (e.g. oral solutions, oral suspensions, oral emulsions, tablets, powders and tablets to extemporarily prepare oral solutions, suspensions or emulsions) or to be applied topically (e.g. creams, ointments, foams, suppositories, gel, spray).

These compositions may moreover include preservatives, ionic and non ionic buffered agents and additives normally used in preparing oral or topical compositions.

The claimed compositions may moreover comprise other natural components useful for the treatment of the mentioned pathologies such as local anesthetics and vasoconstrictive agents (e.g. flavonoids from *Aesculus hippocastanum* extracts, having anti-inflammatory and vasoconstrictive effect, and escin, the active principle from *Aesculus hippocastanum* having vasoprotective, anti-edemigenous and anti-oxidant action and able to stabilize vascular resistance and permeability, currently used in topical and systemic products; extract from *Ruscus aculeates*, rich in substances similar to those found in hippocastanum, able to determine a venotonic, vaso-constrictive and anti-inflammatory action observed in several clinical studies, and polyphenols and flavonoids extract from *Cupressus*, having anti-inflammatory and vaso-constrictive action). These substances rarely produce undesired effects, unlike classical phlebotonic drugs (the main contra-indication for products containing cortisone are, besides pregnancy, bleeding hemorrhoids, especially when there is a blood dripping: in this case, cortisone may delay the healing process and therefore it is better using products free of cortisone.

The most common solvent for liquid compositions, suspensions or emulsions is water or an aqueous solution containing components useful for oral or topical use.

Topical compositions may contain surfactants (e.g. glyceryl monostearate), fat substances (as suppository base), ointment bases (e.g. stearic acid, stearyl alcohol or lanolin), suspending agents (e.g. talc, silicic anhydride), antimicrobial preservatives (e.g. methyl p-hydroxybenzoate, propyl p-hydroxybenzoate or butyl p-hydroxybenzoate), lubricants (e.g. calcium stearate magnesium stearate, aluminum stearate, stearyl acid, stearic acid, cetyl alcohol, palmitic acid, starch or PEG) and substances having a mild antiseptic action (e.g. lavander extract or rosemary extract) and their combinations.

Polysaccharides from *Opuntia Ficus Indica* Cladodes Extract

Chemical structure and compositions of mucilage from *Opuntia Ficus Indica* cladodes was analyzed by several research groups (D. McGarvie, H. Parolis, Methylation analysis of the mucilage of *Opuntia ficus indic*. *Carbohydrate Research*, (1981) 88: 305-314; M. S. Karawya et al. Mucilages and Pectines of *Opuntia, Tamarindus* and *Cyclonia*. *Planta Medica* (1980) Supplement:68-75; M. E. Malainine et al. Structure and morphology of cladodes and spines of *Opuntia ficus* indica. Cellulose extraction and characterisation. *Carbohydrate polymers* (2003) 51:77-83).

Mucilage is deemed to be composed of 1,4-α-D-galactopyranosyluronic acid and 1,2-β-L rhamnopyranosyl residues to which are attached short chains of 1,6-β-D-galacto-pyranosyl residues at position 4 of all of the rhamnopyranosyl residues. Most of the galactosyl residues are branched at O-3, or at O-4, which mainly carry arabinofuranosyl and xylopyranosyl residues.

(D. McGarvie, H. Parolis, Methylation analysis of the mucilage of *Opuntia ficus indic*. *Carbohydrate Research*, (1981) 88: 305-314).

Mucilage from *Opuntia ficus indica* cladodes extract is separated by a simple squeezing process (P. Trombetta et al. Effect of polysaccharides from *Opuntia ficus-indica* (L.) cladodes on the healing of dermal wounds in the rat. *Phytomedicine* (2006) 13: 352-358) or by treatment with water (R. Várz,quez-Ramirez et al. Reversing gastric mucosal alterations during ethanol-induced chronic gastritis in rats by oral administration of *Opuntia ficus-indica* mucilage. *World J Gastroenterol* (2006)12(27):4318-4324).

Extraction Process from *Opuntia Ficus Indica* Cladodes

*Opuntia ficus indica* cladodes are washed and cutted into pieces of about 10 $cm^2$ and then are squeezed by using an hydraulic forging press.

The juice obtained by cladodes squeezing is centrifuged for 15 min at 5000 g and supernatant is ultrafiltered. In this way, an aqueous solution enriched in polysaccharides fraction with MW>10" Da is obtained. This aqueous solution is then concentrated at low pressure and at 35-40° C., and is subsequently dried by spry-drying or freeze-drying.

The analysis of *Opuntia ficus indica* cladodes extract polysaccharides fraction confirmed the presence of arabinose, rhamnose, xylose, galactose and galacturonic acid (D. McGarvie, H. Parolis, Methylation analysis of the mucilage of *Opuntia ficus Indic*. *Carbohydrate Research*, (1981) 88: 305-314). NMR (Nuclear Magnetic Resonance) pointed out a typical structure in polysaccharides from *Opuntia ficus indica*, cladodes. Polyschardes content in *Opuntia ficus indica* cladodes extract is from 1 to 70% w/w.

*Olea Europaea* Leaf Extract

*Olea europaea* leaf extract has a characteristic composition in biophenols, containing simple phenols (tyrosol, hydroxityrosol and derivatives), flavonoids (apigenina, luteolina and their glucosides) and secoridoids (oleuropein and derivatives).

Biophenols are extracted from olive leaf using aqueous or hydro-alcoholic solvents containing ethanol from 10 to 80% v/v (Lee Oil et al. Assessment of phenolics-enriched extract and fractions of olive leaf and their antioxidant activities Bioresour Technol (2009) *Epub ahead of print*; Mylonaki S. et al. Optimisation of the extraction of olive (*olea europaea*) leaf phenolics using water\ethanol-based solvent systems and response surface methodology. *Anal Bioanal Chem*. (2008) 392(5):977-85). Extraction processes are generally carried out at room temperature for avoiding changes or degradation in active susbtances, but in some cases extraction processes may be carried out at temperature up to 60-70° C. Biophenols extraction from plant, matrix may be carried out even using microwaves (Japón-Lujan R, Luque de Castro MD. Small branches of olive tree: a source of biophenols complementary to olive leaf. *J Agric Food Chem*. (2007) 30; 55(11):4584-8), ultrasound (Vassiliki T Papoti, Maria Z. Tsimidou, Impact of sampling parameters on the radical scavening potential of olive (*Olea europaea* L.) leaf. *J Agric Food Chem* 2009, 57, 3470-3477), or superheated liquid extraction (Japón-Luján R, Luque de Castro MD. Superheated liquid extraction of oleuropein and related biophenols from olive leaf, *J Chromatogr A*. (2006) 1136(2):185-91), greatly reducing solvent and plant matrix contact time (from 3 hours to 10 minutes).

Biophenols Extraction from *Olea europaea* Leaf

*Olea europaea* leaf are dried, cutted and then entracted with an ethanol/water 50:50 (v/v) solution, at room temperature for 12 hours. The extraction process is carried out with a 1:5 (g/ml) drug:solvent ratio. When the extraction is completed, the extract is removed and the leaf undergo a second hydroalcoholic extraction process at the same conditions. The extracts are then mixed and the solvent is removed by concentration in vacuum at 40° C. Finally, for increasing biophenols concentration, the extract is adsorbed on styrenic resins and biophenols and then eluted with an ethanol/water 50:50 (v/v) solution.

The extract obtained contains: flavonoids (apigenin, luteolin and their derivatives)2-40%, oleuropein 0.5-10% and hydroxitvrosol and derivatives 1-30%.

Methods to obtain the pharmaceutical or nutraceutical claimed compositions are known in the art. Opuntia *Ficus indica* extracted polysaccharides may be present from 0.5 to 50% of the total compositions, while the other actives may be present from 1 to 30% (w/w or w/v).

The claimed substances are individually applied in the dietary field, so they are safe even for delicate patient's categories, as well as elderly people, children or pregnant women.

The claimed compositions may contain substances from natural sources having astringent action (as well as Hamamelis virginiana extract, zinc oxide or calamine), vasocostrictive agents (e.g. phenylefrine HCl, ephedrine sulfate, epinephrine and epinephrine HCl), steroidal anti-inflammatories (e.g. hydrocortisone), fitosteroids (e.g. flavio enterolignans, coumestrol, beta-sitosterol, ginsenoides), local anesthetics (e.g. benzocaine 5-20%, benzyl alcohol 1-4%, dibucaine 0.25-1%, lidocaine 0.5-5%, pramoxine about 1%, tetracaine 0.5-1%) and their combinations. Preferably, mentioned components are used in their hydrosoluble form (e.g. esters or salts).

The present invention comprises the use of the described compositions for treating and preventing hemorrhoidal diesease relapses administering to a subject therapeutically effective amount of the compositions as defined above, optionally in combination with *Capparis Spinosa* buttons extracts, anthocianosides from red oranges, black rice or from other natural sources and their combinations, for preventing and treating the same diseases.

Non limiting examples of compositions according to the invention are reported in the following tables.

EXAMPLE 1

Compositions

1. Hard capsules:

| Components | mg/capsule |
|---|---|
| *Opuntia Ficus Indica* cladodes extract | 200-400 mg |
| *Olea europaea* leaf extract | 200-400 mg |
| Lactose | Up to capsule filling |

2. Gels:

| Components | % w/w |
|---|---|
| Natrosol (hydroxiethylcellulose) | 1.75 |
| *Opuntia Ficus Indica* cladodes extract | 0.5-10 |
| *Olea europaea* leaf extract | 0.5-10 |
| Propylenglycole | 10.00 |
| Sodium citrate | 0.30 |
| Sodium metabisulfite | 0.50 |
| Disodium edetate | 0.10 |
| Metyl p-idroxybenzoate | 0.20 |
| Propyl p-idroxyibenzoate | 0.05 |
| Distilled water | Up to 100 gr |

3. Suppositories:

| Components | mg/suppository |
|---|---|
| *Opuntia Ficus Indica* cladodes extract | 200-400 mg |
| *Olea europaea* leaf extract | 200-400 mg |
| BHA | 0.15 mg |
| BHT | 0.15 mg |
| Witepsol S 55 | Up to filling |

4. Ointments:

| Components | % w/w |
|---|---|
| *Opuntia Ficus Indica* cladodes extract | 100-200 mg |
| *Olea europaea* leaf extract | 100-200 mg |
| Macrogol 400 | 55 g |
| Macrogol 4000 | 39.9 g |
| Distilled water | Up to 100 g |

EXAMPLE 2

In Vitro Determination of Mucoadhesion of Polysaccharides from *Opuntia Ficus Indica* Cladodes In order to assess the mucoadhesive capability of polysaccharides from *Opuntia Ficus Indica* cladodes the in vitro mucoadhesion assay described by Patel (Patel D, e altri, *An in vitro mucosal model predictive of bioadhesive agents in the oral cavity*, J Control Release, 1999, 61 (1-2): 175-183) was used on suspended intestinal epithelial Caco2 cells, In this test the mucoadhesion (adhesion capability of the tested substances in terms of binding to the mucosal cells) is determined as a function of binding lectin-membrane glycoprotein inhibition determined by the cellular surface hiding due to the mucoadhesive substance.

Materials and Methods

Treatment of mucosal cells with biotinylated lectin and streptavidin peroxidase, determines a yellow colour of the sample; a pre-treatment of mucosal cells with a mucoadhesive substance, (30° C. for 15 minutes before the treatment with lectin), will hide the lectin binding site, reducing the final yellow colouring intensity.

Lectin is a protein contained in some plants of Leguminosae (*Canavcdia ensiformis*), with high tendency to bind glucosidic and mannosidic residues of membrane glycoproteins; biotin (vitamin H) is bonded to lectin following its binding to streptavidin peroxidase that is added to cellular suspension to obtain the complex protein-glucose-lectin-biotin-streptavidin peroxidase.

Figure 1:
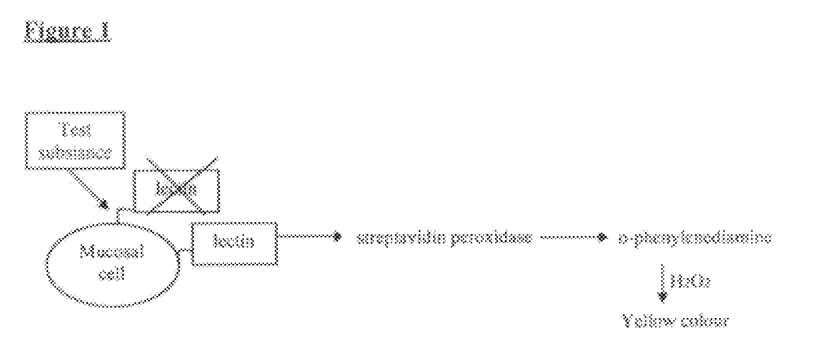
FIG. 1 represents a scheme of the in vitro mucoadhesion model.
Figure 2:
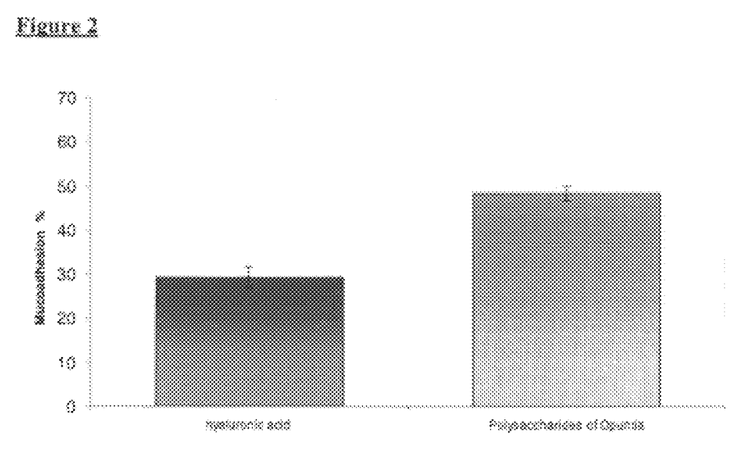
FIG. 2 graphs the comparison of the mucoadhesion percentage values (inhibition percentage of lectin binding after treatment) for *Opuntia ficus indica* cladodes extract versus hyaluronic acid in an in vitro mucoadhesion model on epithelial rectal mucosa cells.

By addition of o-phenylendiamine dihydrochloride (o-pd) and hydrogen peroxide to the cellular suspension, o-pd is oxidized by the complex protein-glucose-lectin-biotin-streptavidin peroxidase to 2,3-diaminophenazine, and the sample becomes yellow (FIG. 2).

The reaction is then blocked after 1 min adding $H_2SO_4$ 1M The colour intensity is read at the spectrofluorimeter and it is proportionally related to binding between lectin and glycosidic residues on cellular membrane.

Caco2 cells were manteined in Minimun Essential Medium (MEM) with 10% fetal calf serum, 100 U/ml penicillin and 100 µg/ml streptomycin at 37° C. and 95:5% air:$CO_2$ conditions. The medium was changed every 2-3 days. Twentyfour hours before treatment, cells were trypsinized, counted using an hemacytometer, centrifuged at 1500 rpm/5 min and resuspended in 2 ml 0.05 M TBS (Tris Buffered Saline) (pH 4).

Polysaccharides from *Opuntia Ficus Indica* cladodes and hyaluronic acid (used as reference substance because of its mucoadhesive properties) were solubilised in NaCl 0.9% solution at 0.5% w\v and these solutions were then used for pre-treatment of the test on Caco2 cells. Results were expressed in percentage of tested substance and mucosa cells binding, inversely proportional to percentage of reduction of sample colouring in comparison to the control.

The whole experiment was repeated 5 times. Statistical analysis of results was performed by means of one-way ANOVA followed by Bonferroni post hoc test.

Results

Figure 3:
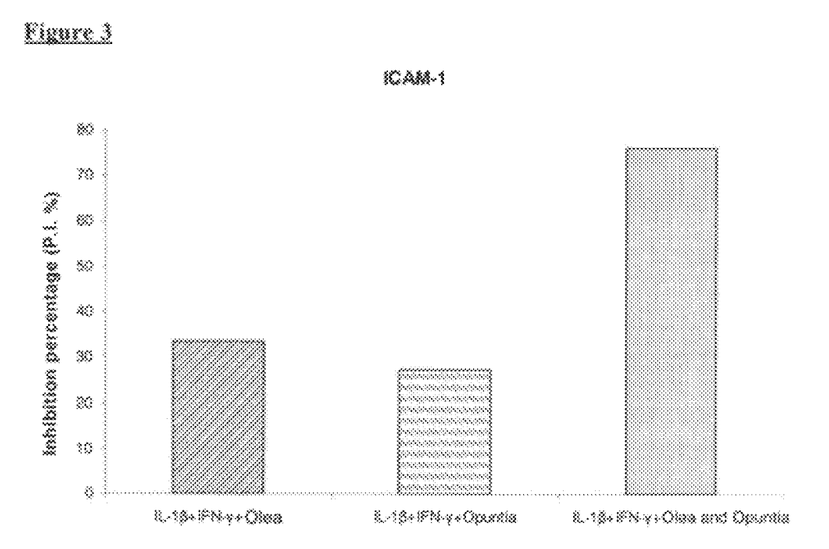
FIG. 3 graphs the ICAM-1 inflammation marker inhibition percentage values determined by polysaccharides from *Opuntia Ficus Indica* cladodes extract and by *Olea europaea* leaf extracs oar Caco2 cells treated with pro-inflammatory substances.

As depicted in FIG. 3, the results obtained with the in vitro mucoadhesion assay on Caco2 suspended cells show an *Opuntia Ficus Indica* polysaccharides mucoadhesion percentage of 48%, significantly higher than that one observed with sodium hyaluronate (mucoadhesion 29%).

Conclusions

The results of the in vitro mucoadhesion assay show that *Opuntia Ficus Indica* cladodes polysaccharides have a strong mucoadhesive character on Caco2 cells. This effect determines, after oral administration or topical rectal application, the formation of a layer able to protect intestinal and rectal mucosa from the irritating effect of some substances which, introduced with foods, may be present in faeces. This effect is useful in hemorrhoidal disease symptom reduction and relapse prevention.

EXAMPLE 3

In Vitro Evaluation of Anti-Inflammatory Activity of *Opuntia Ficus Indica* Cladodes Polysaccharides and *Olea europaea* Leaf Extract In order to assess the anti-inflammatory activity of *Opuntia Ficus Indica* cladodes polysaccharides and *Olea europaea* leaf extract, an in vitro test on Caco2 cells was used.

Caco2 intestinal cells—which are widely used to study gastro-intestinal tract functionality (Sambuy Y. et al., *The Caco-2 cell line as a model of the intestinal barrier: influence of cell and culture-related factors on Caco-2 cell functional characteristics*, Cell Biol Toxicol, 2005; 21(1):1-26; Navarro-Perán E. e altri, *The anti-inflammatory and anti-cancer properties of epigallocatechin-3-gallate are mediated by folate cycle disruption, adenosine release and NE-kappaB suppression*, Inflamm Res. 2008 Oct. 2)—were chosen for their morphological and biochemical characteristics, typical of intestinal enterocyte.

Caco2 cells were stimulated with pro-inflammatory substances. Then the capability of *Opuntia Ficus Indica* cladodes polysaccharides and of *Olea europaea* leaf extract to reduce the inflammation in the intestinal epithelium was determined in terms of intercellular adhesion molecule ICAM-1 and interleukin-8 (IL-8) inflammation markers production. ICAM-1 is an important factor involved in retention of T cells at the inflammed epithelium and represents a significant co-stimulatory signal for CD4 T and CD8 (Ramakers J D e altri, *Arachidonic acid but not eicosapentaenoic acid (EPA) and oleic acid activates NF-kappaB and elevates ICAM-1 expression in Caco-2 cells*. Lipids 2007; 42(8):687-98).

IL-8 is produced by monocytes, fibroblasts, endothelial and epithelial cells during inflammation disorders and is very important for T lymphocytes and neutrophyls recruitment (Vavricka SR e altri, *hPepT1 transports muramyl dipeptide, activating NF-kappaB and stimulating IL-8 secretion in human colonic Caco2/bbe cells*, Gastroenterology 2004; 127(5):1401-9).

Intestinal epithelium inflammation was induced by interleukin-1β (IL-1β) and interferon-γ (IFN-γ), two of the most powerful pro-inflammatory substances (Garat C. e altri, intracellular IL-1Ra type 1 inhibits IL-1-induced IL-6 and IL-8 production in Caco-2 intestinal epithelial cells through inhibition of p38 mitogen-activated protein kinase and NF-kappaB pathways. Cytokine. 2003 Jul.;23(1-2):31-40).

Materials and Methods

Polysaccharides from *Opuntia Ficus Indica* cladodes and from *Olea europaea* leaf extracts were diluted at 100 mg/ml. From this solution, subsequent dilutions were obtained for cell culture treatments.

Cells were manteined in Minimun Essential Medium (MEM) with 10% fetal calf serum, 100 U/ml penicillin and 100 µg/ml streptomycin at 37° C. and 95:5% air:$CO_2$ conditions. The medium was changed every 2-3 days. Twentyfour hours before treatment, cells were trypsinized, counted using an hemacytometer, and then seeded in 96 well plates (for the ELISA test) and 100 mm Petri dishes (for the Western blot).

Afterwards, cells were treated with a mixture of IL-1β (10 ng/ml) and IFN-γ (200 U/ml), and with polysaccharides from *Opuntia Ficus Indica* cladodes and/or with *Olea europaea* leaf extract at 200 µg/ml for 48 hours.

The expression levels of ICAM-1 were determned by Western blot, while IL-8 was determined by ELISA test. The results were expressed as percentage of inflammation markers inhibition in cells treated with polysaccharides from *Opuntia Ficus Indica* cladodes and/or with *Olea europaea* leaf extract versus cells treated IL-1β and IFN-γ.

—Western Blot

Proteins were extracted from cells 48 hours after treatment, loaded on a 4-12% polyacrylamide gel, transferred to a nitrocellulose membrane and incubated with a monoclonal antibody to ICAM-1. The protein expression was quantified by densitometric analysis of autoradiographs and values were expressed as arbitrary densitometric units corresponding to the intensity of the signal.

The results were normalized with the levels of α-tubulin as reference protein for loading control.

—ELISA

IL-8 was measured in the supernatant free from cells harvested 48 hours after treatment using an ELBA. kit (Enzyme-Linked Immunosorbent Assay) able to specifically recognize the protein by antigen-antibody binding. The complex is recognized and bound by a polyclonal antibody labeled with an enzyme. Calculating the enzyme activity after the addition of substrate, it is possible to have an estimate directly proportional to the amount of test antigen. Values are reported as pg/ml±SEM.

Results

Figure 4:
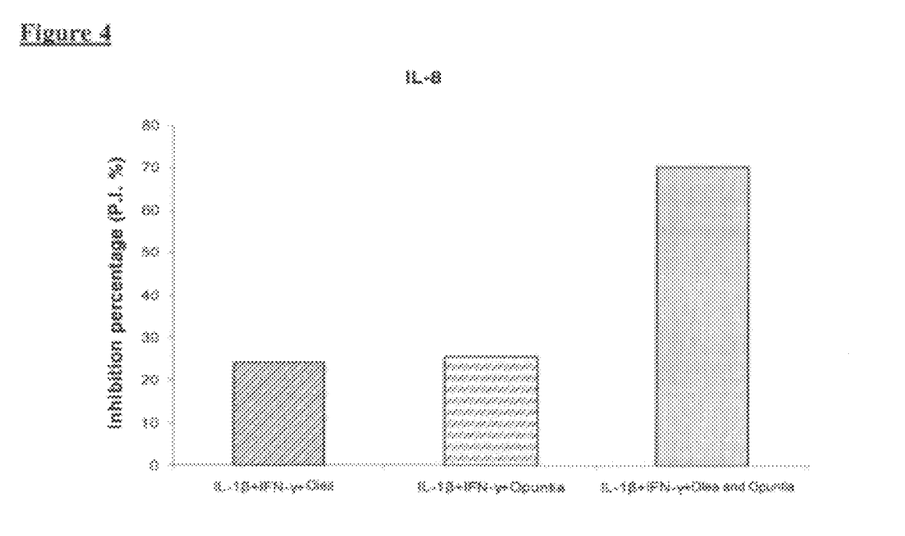
FIG. 4 graphs the IL-8 inflammation marker inhibition percentage values determined by polysaccharides from *Opuntia ficus indica* cladodes extract and by *Olea europaea* leaf extracs on Caco2 cells treated with pro-inflammatory substances.

The results obtained with Wester blot conducted on Caco2 cells show that polysaccharides from *Opuntia Ficus Indica* cladodes and *Olea europaea* leaf extracts determine respectively a inhibition percentage of 27% e al 33% (FIGS. 3 and 4).

The ability to inhibit expression of IL-8 in the same cell culture, determined by ELISA, was found to be 26% for polysaccharides from *Opuntia Ficus Indica* cladodes and 24% for *Olea europaea* leaf extract (FIG. 4).

Moreover, in both the experiments, the treatment of Caco2 cells with a combination of polysaccharides from *Opuntia Ficus Indica* cladodes and *Olea europaea* leaf extracts show a synergistic effect in percentage of inhibition of both ICAM-1 (76%) and IL-8 (70%, Figgs 3 and 4).

Conclusions

The in vitro test shows that *Olea europaea* leaf extract determines an unexpected synergistic effect in the anti-inflammatory action of polysaccharides from *Opuntia Ficus Indica* cladodes extract, particularly a synergistic effect in reducing the expression of both the markers of inflammation ICAM-1 and IL-8 induced in Caco2 cells by using pro-inflammatory substances.

The experimental data show that polysaccharides from *Opuntia Ficus Indica* cladodes extract have a mucoadhesive action and an anti-inflammatory action. The latter is quite unexpectedly enhanced in a synergistic way by *Olea europaea* leaf extract.

Both those effects are useful for prevention and treatment of hemorrhoidal disease, its complications and related illnesses.

The invention claimed is:

1. A method of treating hemorrhoidal disease, in patients in need thereof, said method comprising:
   administering an effective amount of a composition containing an extract of *Opuntia ficus indica cladodes* and an extract of *Olea europeae* leaves to patients suffering from said hemorrhoidal disease, wherein the *Opuntia ficus indica* extract contains from 1 to 70% w/w polysaccharides, enriched in the MW>104 Da polysaccharides fraction and wherein the *Opuntia ficus indica* cladodes polysaccharides are in amounts from 0.5% to 50% w/w and the extract of *Olea europeae* leaves are in amounts from 1% to 30% (w/w), the weight ratio of *Opuntia ficus indica* cladodes polysaccharides to extract of *Olea* leaves in the composition being 1:1.

2. Method according to claim 1, comprising administering a composition further containing extracts from *Capparis Spinosa* buttons, anthocianosides from red oranges, black rice or from other natural sources and their combinations.

3. Method according to claim 1, comprising administering a composition further containing one or more ingredients selected from local anesthetic, anti-inflammatory substances having astringent action, vasocostrictor agents, steroidal anti-inflammatories and their combinations.

4. Method according to claim 1, wherein the *Opuntia ficus indica* extract contains polysaccharides in mucilage form.

5. Method according to claim 1, wherein the *Olea europaea* leaf extract is obtained by treating *Olea* leaf with aqueous or hydroalcoholic solvents at room temperature or heating up to 60-70° C., optionally repeating the extraction process and then eliminating the solvent in vacuum at 40° C.

6. Method according to claim 1, wherein said composition is suitable for oral, intrarectal or topical administration.

7. Method according to claim 6, wherein said composition is in the form of oral solution, oral suspension, oral emulsion, tablets, capsules, powders and bags for the extemporary preparation of oral suspensions or oral emulsions, creams, ointments, foams, gels, spray preparations, suppositories.

8. Method according to claim 7 wherein said composition is selected from:

i) capsule having the following composition:

| Components | mg/capsule |
| --- | --- |
| *Opuntia Ficus Indica* cladodes extract | 200-400 mg |
| *Olea europaea* leaf extract | 200-400 mg |
| Lactose | Up to capsule filling | ii) topical/intrarectal gel having the following composition:

| Components | % w/w |
| --- | --- |
| Natrosol (hydroxiethylcellulose) | 1.75 |
| *Opuntia Ficus Indica* cladodes extract | 0.5-10 |
| *Olea europaea* leaf extract | 0.5-10 |
| Propylenglycole | 10.00 |
| Sodium citrate | 0.30 |
| Sodium metabisulfite | 0.50 |
| Disodium edetate | 0.10 |
| Metyl p-idroxybenzoate | 0.20 |
| Propyl p-idroxyibenzoate | 0.05 |
| Distilled water | Up to 100 gr | iii) suppository having the following composition:

| Components | mg/suppository |
| --- | --- |
| *Opuntia Ficus Indica* cladodes extract | 200-400 mg |
| *Olea europaea* leaf extract | 200-400 mg |
| BHA | 0.15 mg |
| BHT | 0.15 mg |
| Witepsol S 55 | Up to filling | and iv) ointment having the following composition:

| Components | % w/w |
| --- | --- |
| *Opuntia Ficus Indica* cladodes extract | 100-200 mg |
| *Olea europaea* leaf extract | 100-200 mg |
| Macrogol 400 | 55 g |
| Macrogol 4000 | 39.9 g |
| Distilled water | Up to 100 g. |

9. Method according to claim 3, wherein said anti-inflammatory substances are selected from *Aesculus hippocastanum, Ruscus aculeatus* and *Cupressus* extracts, said fitosteroids, substances having astringent action are selected from *Hamamelis virginiana* extract, zinc oxide and calamine and said vasocostrictor agents are selected from phenylefrine HCl, efedrine sulfate, epinefrine and epinefrine HCl.

* * * * *